Feb. 4, 1958 P. F. DE VOR Plant Pat. 1,677
RED ROSE PLANT
Filed June 25, 1957
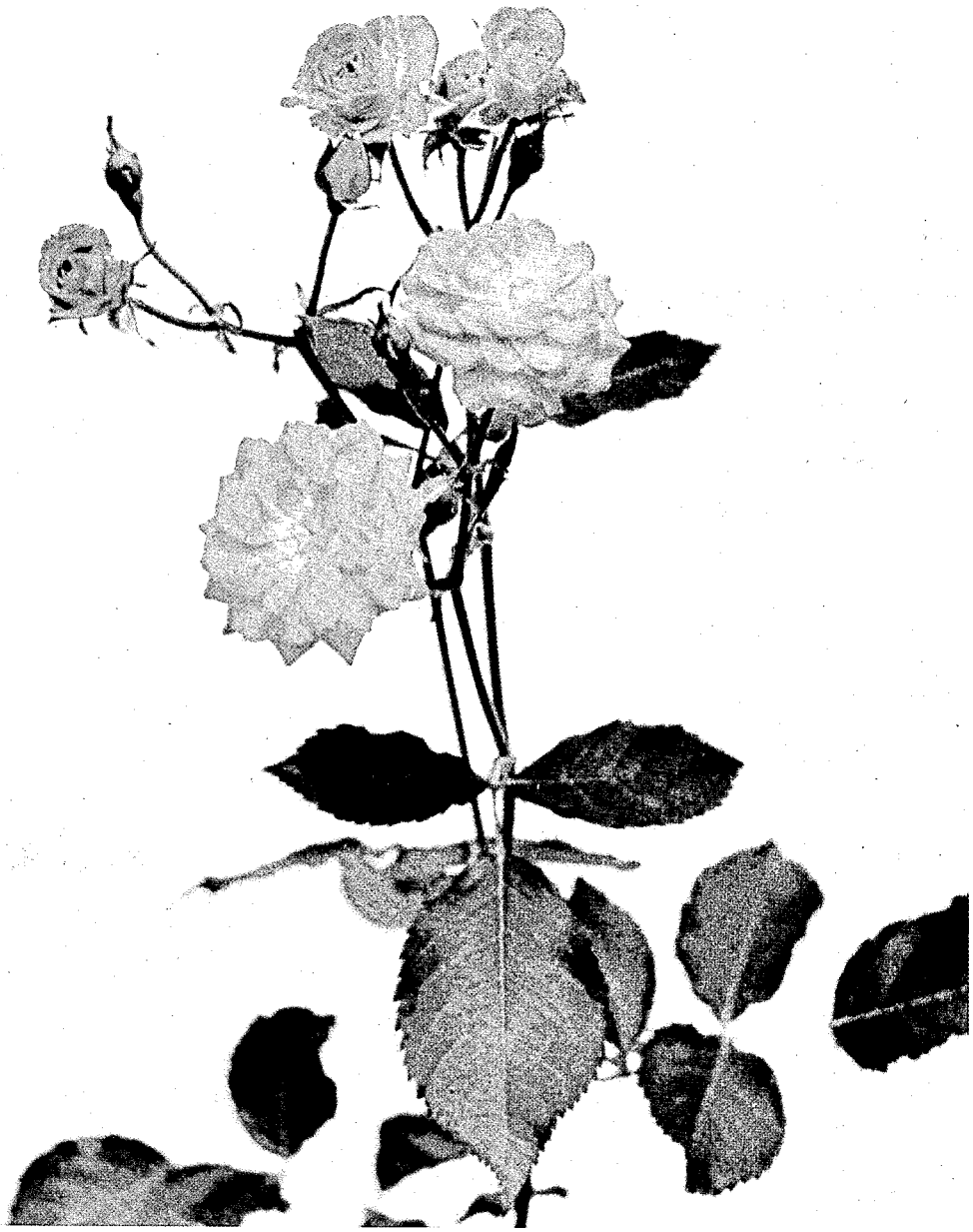
INVENTORS:
PAUL F. DeVOR
BY Kenmuler & Snow
ATT'YS United States Patent Office Plant Pat. 1,677
Patented Feb. 4, 1958

1,677

RED ROSE PLANT

Paul F. De Vor, Pleasanton, Calif., assignor to Clarence Amling Roses, Inc., Santa Ana, Calif., a corporation of California Application June 25, 1957, Serial No. 668,006

1 Claim. (Cl. 47—61)

My present discovery is of a new and distinct variety of rose plant, which originated as a sport of my own unnamed variety of hybrid polyantha pink rose plant, described and illustrated in my copending application Serial Number 668,007 filed June 25, 1957, which latter variety originated as a sport of the variety Carol Amling (Plant Patent Number 1,126), this new variety having been discovered by me at Livermore, California. Asexual reproduction by budding under my direction has proved the new variety to reproduce true to form.

This new sport, which is a hybrid polyantha, commercially classified as floribunda, exhibits a very beautiful rearrangement and accentuation of the characteristics which are found in the plant disclosed in my said copending application; in the variety "Carol Amling" (Plant Pat. 1,126), and in the variety "Garnette" (unpatented).

The flower of this new variety is a reversion to "Garnette" in that its color is more similar and the regularly imbricate petal arrangement is practically identical.

The bud of this new variety, however, is urn-shaped and high centered, like the bud of my before mentioned co-pending application, which is one of the chief attractions of each of these new varieties, and the smaller diameter of the bud of this new variety, when first opening, gives it an even more exquisite shape.

The blooms of this new variety, though averaging more flowers per cluster than the plant disclosed in my co-pending application, occur on branches which are also more spreading in habit, diverging from the center of the plant, and thus giving it an even more graceful informal appearance. In this respect this new variety is an even further departure from the flower and plant habit of "Garnette" than is its parent plant, and especially the variety "Carol Amling" from which its parent originated.

The leaves of this new variety are practically the same in shape, size and color as its parent plant; but there are more of them per foot of plant stem and in this respect it is similar to "Carol Amling" and "Garnette."

The plant of this new variety is much more willowy and spreading in habit than that of its parent and somewhat less vigorous. It is slightly more thorny than the parent plant, but still less thorny than either "Carol Amling" or "Garnette." In body structure this new variety may be characterized as a "Garnette" type of flower both as to color and form. It is comparable to "Garnette" in keeping quality. But the lovely urn-shaped, high centered bud sharply distinguishes it from "Garnette."

The accompanying illustration is a full color photograph showing the flowers, stems and foliage of the new variety. The flowers are shown in various stages from bud to full bloom and the colors shown are substantially true to the color designations hereafter set out.

The following is a detailed description of my new variety of rose plant and all color designations therein are according to the Horticultural Color Chart of the British Horticultural Council.

Classification: Botanic—hybrid polyantha. Commercial—floribunda.

*Flower*

Blooming habit: Continuous. Blooms profusely from spring until fall.

Size: Medium. Diameter, 2¼–2¾ inches. Depth, ¾–1 inch.

Borne: In clusters. 3 to 8 flowers, often compounded into clusters of 25 to 30 flowers.

Shape: High center, regularly imbricate when bloom opens. Form does not change later.

Petalage: 41 to 58 petals plus 4 to 11 petaloids.

*Form.*—Oblong-lanceolate-ovate. Not serrated.

*Color.*—Outer petals—Rose Red (724). Base—Primrose Yellow (601/3). Inside petals—Rose Red (724). Reverse side—Solferino Purple (26). Petals remain on stem 12–15 days.

Petaloids: 4 to 11.

*Size.*—¼" to ⅜" x ¾" to 1 inch.

*Color.*—Same as petals.

Peduncle:

*Length.*—1¼ to 2 inches. Sturdy and upright.

*Color.*—Pod Green tinged with reddish brown anthocyanin toward bud.

Discoloration (after full bloom): Fades to Tyrian Purple (727/2) especially toward ends of petals.

Texture: Soft.

Appearance: Satiny. Color fades more rapidly in hot weather. Petals hang on and dry.

Fragrance: Very slight.

Lasting quality: On plant—6 to 8 days. As a cut flower—9 to 10 days.

*Bud*

Size: ⅞ to 1⅛ inches long.

Form: High centered and urn-shaped.

Diameter: ¾ to ⅞ inches.

Depth: ⅞ to 1⅛ inches high from base. Opens slowly.

Color: When sepals first divide—Dark Rose Red (724). When petals begin to unfurl—Rose Red (724).

Sepals: Curl back and are spear-shaped. Color: inside—Sage Green (000861/2); outside—near Maroon (1030/1).

Calyx: Funnel-shaped. Small and smooth. Does not split. Glandular—margins of sepals with many glandular hairs, some also on outer surface at sepals.

Peduncle: Length—1¼ to 2 inches. Slender and erect. Not hairy, except for small gland-tipped hairs.

*Plant*

Form: Medium-sized bush. Strong grower. Sturdy.

Height: 3 to 3¼ feet.

Growth: Spreading and vigorous.

Branching: Profuse.

Foliage: Ample. Number of leaves—4 per foot of stem.

*Size of leaf.*—3¾ to 4 inches x 5 to 5½ inches.

*Shape.*—Elongate.

*Texture.*—Glossy. Serrated but definitely not as much so as "Garnette" which has much deeper serrations.

*Color.*—Upper side—near Spinach Green (0960). Under side—Sage Green (00861).

*Leaflets.*—1⅛ to 1½ x 1¼ to 2⅛ inches. Number, 5–7.

*Petioles.*—Lengths—¾ to 1¼ inch.

*Ribs and veins.*—Prominent.

*Rachis* with 1 to 3 small (1/16 in.) prickles. Has both thorns and prickles toward base of plant but cutting stems are free of thorns and relatively free of prickles. Thorns are light green in color and ⅜ to ½ inch long.

Genital organs:

*Stamens; anthers.*—Arrangement regular. Length —1/16 inch long. Number—many, 50–60.

*Filaments.*—Length—1/16 to 5/16 inch. Color—Aureolin (3).

*Pollen.*—Color—Aureolin (3–3/2).

*Pistils.*—Number—25 to 35. Length—3/8 to 1/2 inch.

*Stigmas.*—Color—Canary Yellow (2/3).

*Characteristics of ovaries.*—Small, elongate, silvery haired.

*Fruit.*—Very fertile. Shape—round to ovate. Color at maturity—orange-yellow.

Although my new variety more nearly resembles "Garnette" than any other well-known rose, it is distinctly and outstandingly different from "Garnette" especially with respect to the larger number of flowers in each cluster. It is of a more vigorous constitution, relatively thornless, and remains more attractive longer in its open bud and flower stages than "Garnette" and keeps fully as long.

Having thus disclosed my invention, I claim:

A new and distinct variety of rose plant, substantially as herein described, characterized by the high-centered, urn-shaped narrow bud, its large number of rose-red flowers per cluster, the slow opening of the bud and flower, its relative thornlessness, its spreading and willowy habit of growth, and the lasting quality of the blooms on the plant and as cut flowers.

No references cited.